United States Patent [19]

Broquet et al.

[11] Patent Number: 5,972,940
[45] Date of Patent: Oct. 26, 1999

[54] ARGININE ANALOGUES HAVING NITRIC OXIDE SYNTHASE INHIBITOR ACTIVITY

[75] Inventors: Colette Broquet, Boulogne; Pierre Etienne Chabrier De Lassauniere, Paris, both of France

[73] Assignee: Societe de Conseils Recherches et d'Applications Scientifiques (S.C.R.A.S.), France

[21] Appl. No.: 08/913,455

[22] PCT Filed: Mar. 4, 1996

[86] PCT No.: PCT/FR96/00337

§ 371 Date: Sep. 10, 1997

§ 102(e) Date: Sep. 10, 1997

[87] PCT Pub. No.: WO96/27593

PCT Pub. Date: Sep. 12, 1996

[30] Foreign Application Priority Data

Mar. 4, 1995 [GB] United Kingdom .................. 9504350

[51] Int. Cl.$^6$ ...................... A61K 31/535; C07D 233/61; C07D 295/15; C07C 279/14
[52] U.S. Cl. ........................ 514/238.5; 514/315; 514/399; 514/634; 544/162; 544/399; 546/246; 548/334.1; 548/336.1; 548/300.1; 548/375.1; 548/356.1; 548/561
[58] Field of Search .............................. 544/162; 546/245, 546/246; 548/334.1, 336.1; 564/240; 514/238.5, 315, 399, 634

[56] References Cited

U.S. PATENT DOCUMENTS

| | | | |
|---|---|---|---|
| 3,978,045 | 8/1976 | Okamoto et al. | 540/483 |
| 4,133,880 | 1/1979 | Okamoto et al. | 514/183 |

FOREIGN PATENT DOCUMENTS

| | | |
|---|---|---|
| 2320088 | 8/1979 | France . |
| 2656220 | 12/1990 | France . |
| 2263111 | 7/1993 | United Kingdom . |
| 91/04024 | 4/1991 | WIPO . |
| 93/24126 | 12/1993 | WIPO . |

OTHER PUBLICATIONS

Etemad—Moghadam et al., Eur. J. Med. Chem. 23 pp. 577–585, 1988.
Stock, Z. NaturforschTeil C, 28, pp. 319–321, 1973.
Weitzel et al in Hope–Seyler's Z. Physiol. Chem., 353, pp. 1661–1670, 1972.
Ferrario et al, Synthetic Communications, 21, pp. 99–105, 1991.
Kinjo et al, Origins of Life, 14, pp. 351–357, 1984.
Kikumoto et al. Biochemistry 23, pp. 85–90, 1984.
Weitzel et al, Chemical Abstracts, vol. 77, No. 29320, 1972.
Whittle, European Journalof Gastroenterology & Hepatology, vol. 9 pp. 1026–1032, 1997.

Primary Examiner—Emily Bernhardt
Attorney, Agent, or Firm—Bierman, Muserlian and Lucas

[57] ABSTRACT

A compound selected from the group consisting of a compound of the formula

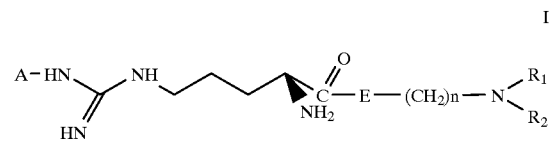

wherein A is selected from the group consisting of hydrogen, alkyl of 1 to 6 carbon atoms and $-NO_2$, E is $-O-$ or a covalent bond, n is an integer from 1 to 12, $R_1$ and $R_2$ are individually alkyl of 1 to 6 carbon atoms or taken together with the nitrogen to which they are attached form an optionally unsaturated 5 to 6-member ring of the formula $-NX$ and X is selected from the group consisting of oxygen, sulfur, methylene and $>N-R'$, R' being hydrogen or an alkyl of 1 to 6 carbon atoms, and their pharmaceutically acceptable acid addition salts useful to inhibit $-NO$ synthase.

5 Claims, No Drawings

ARGININE ANALOGUES HAVING NITRIC OXIDE SYNTHASE INHIBITOR ACTIVITY

The invention concerns derivatives of L-arginine, a procedure for their preparation and pharmaceutical compositions containing them.

The compounds of the invention have a biological activity as inhibitors of the NO synthase. Taking into account the potential role of NO synthase in physiopathology (S. Moncada, R. M. J. Palmer et al, Nitric Oxide: Physiology, Pathophysiology, and Pharmacology. Pharmaceutical Reviews, vol. 43, number 2, pp. 109–142), such compounds may thus be interesting as hypotension, antibacterial, immunosuppressant, antiarterosclerotic, vasotropic, analgesic, antimigraine, ophthalmological, or antidiabetic agents. Thus one may consider using these compounds as the active principle of a medication for the treatment of pathologies of the central and peripheral nervous system such as: cerebral infarctus, migraine and headaches, epilepsy, cerebral or spinal trauma, neurodegenerative and/ or autoimmune diseases such as Alzheimer's disease, Parkinson's disease, Saint Vitus' dance, amyotrophic lateral sclerosis, infectious cerebral neuropathies (AIDS), acute and chronic pain, tolerance to and dependence upon morphine derivatives, psychotropic drugs and alcohol, occular neuropathy, and depression. One may likewise consider using them for other pathologies such as those related to dysfunctions of the gastrointestinal and urinary system of the inflammatory type or not like ulcerous colitis, gastritis, Chronn's disease, urination troubles, esophagus gastro reflux, diarrhea, but also for pathologies connected to the cardiovascular or bronchopulminary system such as hypertension, atherosclerosis, pulmonary fibrosis, sclerodermia, asthma, pulmonary hypertension, cirrhosis, diabetes, for inflammatory or infectious diseases such as arthrosis, polyarthritis, septic shock, vasculitis, or even for troubles of erection, priapism, or contraception.

The invention concerns the derivatives of L-argkdfle of the general formula I:

in which:
A represents a hydrogen atom, a lower alkyl group, or the nitro radical;
E represents an oxygen atom or a covalent bond;
n is equal to zero or an integer from 1 to 12; and,
either $R_1$ and $R_2$ represent independently a branched or linear lower alkyl chain, or $R_1$ and $R_2$ form with the nitrogen atom to which they are attached, a ring of 5 or 6 groups, saturated or unsaturated, of the formula:

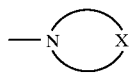

in which X represents an atom of oxygen, of sulfur, or of nitrogen, the imino, alkylimino, or methylene radical, with the exception of general formula I compounds in which n is equal to zero. E represents a covalent bond and either A represents the hydrogen atom and $R_1$ and $R_2$ represent independently a lower alkyl radical or form together the piperidine, morpholine, or imidazole ring, or A represents the nitro radical and $R_1$ and $R_2$ form the piperidine ring.

By lower alkyl is meant the alkyl radicals containing from 1 to 6 carbon atoms. This preferably concerns alkyl radicals, linear or branched, containing from 1 to 4 carbon atoms chosen from among the methyl, ethyl, n-propyl, isopropyl, n-butyl, isobutyl, or ter-butyl groups.

$R_1$ and $R_2$ may form together with the nitrogen atom to which they are attached, a ring with 5 or 6 groups, saturated or unsaturated. The rings thus formed may be chosen from among pyrrole, piperidine, pyrrolodine, imidazole, imidazolidine, pyrazole, pyrazolidine, pyridine, piperazone, pyrazine, pyrimidine, pyridazine, isothiazole, or morpholine.

The invention concerns more particularly the compounds of general formula I in which n is an integer from 1 to 12, and preferably when E represents the oxygen atom, A represents the nitro radical or the hydrogen atom, and $R_1$ and $R_2$ form the morpholine, piperidine, or imidazole ring. The invention concerns more particularly likewise the compound of general formula I in which n is equal to zero, E represents a covalent bond, A the nitro radical, and $R_1$ and $R_2$ form the morpholine ring.

The invention likewise concerns pharmaceutically acceptable salts of the derivatives according to the invention. The salts are formed from organic or inorganic acids such as hydrochloric acid, hydrobromic acid, acetic, fumaric, sulfonic, toluenesulfonic, maleic, carboxylic, or phosphoric acid. The carboxylic acids may be chosen for example from among the acids acetyl salicylic, salicylic, mefenamic, ibruprofen, sulindac, or indomethacine.

Compounds of general formula I in which n is equal to zero, E represents a covalent bond and either A represents the hydrogen atom, $R_1$ and $R_2$ form together the piperidine or morpholine ring, or A represents the nitro radical and $R_1$ and $R_2$ form the piperidine ring, have been described in the literature. In these documents (European Journal of Medicinal Chemistry, vol. 23, No. 6 (1988), Biochemistry, vol. 23, No. 1 (1984), patent applications FR 2320088 and FR 2240720), these derivatives have been used for the preparation of derivatives of L-arginine as anti-thrombotics. The compound of formula I in which n is equal to zero, E represents a covalent bond, A represents the hydrogen atom and $R_1$ and $R_2$ form together the imidazole ring is described as a synthesis intermediary (Origins of Life, vol. 14 (1984), pp. 351–357). However, no pharmacological activity has been attributed to these products. The activity of other formula I derivatives in which n is equal to zero, E represents a covalent bond, A represents the hydrogen atom and $R_1$ and $R_2$ represent independently a lower alkyl radical was compared with that of insulin (Z. Naturforsch. Teil C., vol. 28, No. 5–6, 1973; Hope-Seyler's Z. Physiol. Chem., vol. 353, #11, 1972, pp. 1661–1670). But the domains of thrombosis and of diabetes are very different from the domain of NO synthesis covered by the present invention.

The invention concerns a procedure for preparing general formula I compounds, which procedure consists of causing the reaction of a compound of general formula (2):

(2)

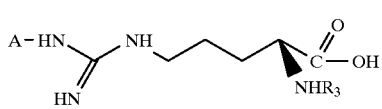

in which A represents a lower alkyl radical or the nitro radical and $R_3$ a protector group, with a compound of general formula (3):

  (3)

in which n, E, $R_1$, and $R_2$ are as defined above, in the presence of a coupling agent, at a temperature ranging between 0 and 30 degrees C., then to cleave the protecting group $R_3$ of the compound thus obtained from the general formula (4):

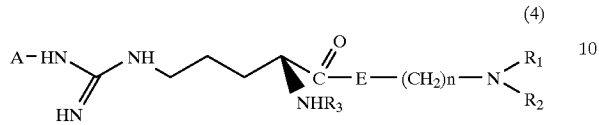  (4)

to obtain the compound of the general formula I in which A represents the nitro radical or a lower alkyl radical. If one desires to obtain a compound of general formula I in which A represents a hydrogen atom, one uses the corresponding compound of general formula I in which A represents the $NO_2$ radical and the nitro radical is cleaved: the cleavage may be done by hydrogenolysis.

The starting compounds (3) and (2) in which A represents the nitro radical are known and marketed: the compounds (2) in which A represents a lower alkyl radical may be prepared according to known methods (Synth. Commun. 21 (1), 99 (1991). The first stage is done at a temperature ranging between 0 and 30 degrees C. and preferably between 0 degrees C. and ambient temperature. The solvent used must dissolve the derivative of the nitroarginine of formula II: preferably, DMF is used. The reaction is conducted by using a coupling agent. An agent chosen from among the coupling agents commonly used in peptide synthesis would work; thus one may use N,N'-dicyclohexyl carbodiimide (DCC), benzotriazol-1-yl-oxy-tris(dimethyl-aminophosphonium hexafluorophosphate (BOP) or benzotriazol-1-yl-oxy-tris-pyrrolidinophosphonium hexafluorophosphate (PyBOP). Additives may likewise be used with the coupling agent as for example 1-hydroxybenzotriazol (HOBt) or 4-dimethylaminopyridine (DMAP) which are known in peptide synthesis to accelerate coupling in which carbodiimide plays a part.

The protector group $R_3$ may be any of the protector groups commonly used in peptide synthesis such as benzyloxycarbonyl (Z) and t-butoxycarbonyl (BOC). During the preparation of a compound I in which A represents a hydrogen atom, the radical $R_3$ is preferably a radical which may be cleaved under conditions of hydrogenolysis for the cleavage of the nitro radical. In this way the cleavage of the radical $R_3$ and of the nitro radical may be conducted simultaneously.

The invention also concerns pharmaceutical compounds including by way of active principle at least one compound of general formula I:

in which:

A represents a hydrogen atom, a lower alkyl group, or the nitro radical;

E represents an oxygen atom or a covalent bond;

n is equal to zero or an integer between 1 and 12; and, either $R_1$ and $R_2$ represent independently a branched or linear lower alkyl chain or $R_1$ and $R_2$ form together with the nitrogen atom on which they are attached a ring of 5 or 6 groups, saturated or unsaturated, of the formula

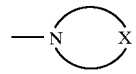

in which X represents an atom of oxygen, of sulfur, or of nitrogen, the imino, alkylimino, or methylene radical, with the exception of compounds of the general formula I in which n is equal to zero, E represents a covalent bond and either A represents the hydrogen atom and $R_1$ and $R_2$ represent independently a lower alkyl radical or form together the imidazole, morpholine, or piperidine ring, or A represents the nitro radical and $R_1$ and $R_2$ form the piperidine ring, or a salt of these compounds in association with at least one diluting agent or pharmaceutically acceptable vehicle.

The invention likewise concerns pharmaceutical compositions containing by way of active principle at least one compound of formula $I_A$:

in which:

A represents an atom of hydrogen, a lower alkyl group, or the nitro radical;

E represents an atom of oxygen or a covalent bond;

n is equal to zero or an integer between 1 and 12; and, either $R_1$ and $R_2$ represent independently a branched or linear alkyl chain, or $R_1$ and $R_2$ form together with the nitrogen atom to which they are attached a ring of 5 or 6 groups, saturated or unsaturated, of the formula

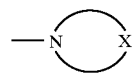

in which X represents an atom of hydrogen, of sulfur or of nitrogen, the methylene, alkylimino, or iniino radical, with the exception of compounds of the general formula $I_A$ in which n is equal to zero, E represents a covalent bond, A represents the hydrogen atom and $R_1$ and $R_2$ represent independently a lower alkyl radical or a salt of these compounds in association with at least one diluting agent or pharmaceutically acceptable vehicle.

The pharmaceutical compositions according to the invention are adapted to the chosen mode of administration, especially oral and parenteral. They may thus be for example in the form of capsules, pills, gels, drinkable solutions, injectable solutions, or in a form adapted to prolonged release. The compounds according to the intention may be administered at a dose ranging between 0.1 and 1000 mg per day. Preferably the compounds may be administered at a dose ranging between 1 and 100 mg.

The invention concerns finally the use of derivatives of L-arginine of a general formula $I_B$:

in which:

A represents an atom of hydrogen, a lower alkyl group or the nitro radical;

E represents an atom of oxygen or a covalent bond;

n is equal to zero or an integer between 1 and 12; and, either $R_1$ and $R_2$ represent independently a branched or linear alkyl chain; or $R_1$ and $R_2$ form together with the nitrogen atom to which they are attached a ring of 5 or 6 groups, saturated or unsaturated, of the formula

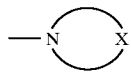

in which X represents an atom of hydrogen, of sulfur, or of nitrogen, the methylene, alkylimino, or imino radical for the preparation of a medication for the treatment of pathologies of the central and peripheral nervous system, of pathologies of diseased of the gastrointestinal and urinary system of the inflammatory type or not, or of pathologies connected to the cardiovascular or bronchopulmonary system.

The invention is illustrated by the following examples:

EXAMPLE 1

Morpholinoethyl Ester of L-$N^G$-nitroarginine (L-NNA):

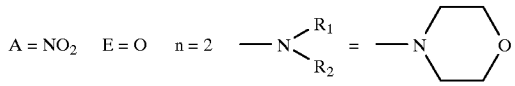

1st Stage:

An equimolecular mixture ($10^{-2}$ M) of L-N-Boc-$N^G$-nitroarginine and N-B-hydroxyethyl morpholine is dissolved in 30 ml of anhydrous dimethyl formamide (DMF), then $3 \times 10^{-3}$ M of dimethylaminopyridine (DMAP) is added. The solution is cooled to 0 degrees C. and $10^{-2}$ M of dicyclohexyl carbodiimide (DDC) is added. It is stirred at 0 degrees C. for 10 minutes, then the stirring is continued at room temperature for 24 hours. The precipitate of dicyclohexyl urea formed is filtered and the solvent eliminated. The residue is recovered by ethyl acetate, then washed once with water and once with saturated NaCl. The elimination of the solvent leaves a viscous product which is chromatographed on a silica column (eluant CHCl3/MeOH9595 then 90:10); the compound (4) is obtained in the form of an oil which crystalizes.

Melting point: 128 degrees C. CCM: rf: 0.38 (CHCl$_3$/EtOH 85:15). I.R. (cm$^{-1}$) nujol γ-NH: 3400–3200; γ-ester: 1740; γ-BOC: 1710. Mass spectrum: MH+=433. RMN$^{-1}$H, 100 MHz, CDCl$_3$, TMS, δppm: 7.8 (2H NH$_2$): 5.5 (d. 1H. NHBoc): 4.3 (m. 3H. CH NHCO. CO$_2$CH$_2$); 3.8–3.2 (m. 7H. CH$_2$NH. CH$_2$—O—CH$_2$.NH); 2.5 (m. 6H. 3CH$_2$N; 1.7 (m. 4H. CH$_2$CH$_2$); 1.4 (sing, 9H. tBu).

2nd Stage: Deprotection of the NH$_2$ Function.

The compound (4) obtained in the previous stage is dissolved in anhydrous dioxane; an excess of 4N HCl is added drop by drop in dioxane at ambient temperature. The solution becomes cloudy, then is stirred vigorously for 15 hours until a white precipitate slowly forms. The dioxane is decanted; it is washed twice with anhydrous ether, and it is dried with the rotavapor. The solid is dissolved in water and lyophilized. The compound I is obtained in the form of dichlorohydrate.

F: 230 degrees C.—hygroscopic white powder. CCML:rf: 0.39 (2-propanol/H$_2$O)/NH$_4$OH:7:3:0.1). MH+ (base)=333 [α$_D^{20}$]=+3.81 (H$_2$O) RMN$^{-1}$H, 100 MHz, D$_2$O, δppm: 4.5 (m. 2H. CO$_2$CH$_2$): 4.1 (t, 1H. CH(NH$_2$)CO); 3.7(m. 4H, CH$_2$OCH$_2$); 3.4–3.1 (m. 8H. CH$_2$N): 1.9–1.5 (solid 4H, CH$_2$—CH$_2$).

EXAMPLE 2

Piperidinoethyl Ester of L-NNA

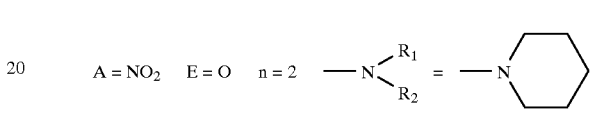

1st Stage:

The corresponding compound of general formula (4) is obtained according to the method as described in example 1, 1st stage, using N-(β-hydroxyethyl)- piperidine instead of N-(β-hydroxyethyl)-morpholine).

White solid—melting point: 98 degrees C. CCM:rf: 0.22 (CHCl$_3$/EtOH 8:2) RMN$^{-1}$H 100 MHz, CDCl$_3$, TMS δpp 7.6 (2H. NH$_2$); 5.5 (t. 1H. NHBoc); 4.3 (t, 3H. CH—NHCO and CO$_2$CH$_2$); 3.4 (solid, 3H. CH$_2$NH. NH); 2.7–2.3 (solid, 6H. 3CH$_2$N): 1.7–1.4 (solid, 19H. tBu and 5CH$_2$).

2nd Stage:

The compound is obtained in the form of dihydrochloride following the method as described in example 1, 2nd stage.

Melting point: 250 degrees C.—hygroscopic white solid CCM:rf: 0.36 (2-propanol/H$_2$O/NH$_4$OH:7:3:0.1) MH+=331 (base) [α$_D^{20}$]=+5.78(H$_2$O) RMN$^{-1}$H, 100 MHz, D$_2$O, δppm: 4.5 (m. 2H. CO$_2$CH$_2$); 4.1 (t. 1H. CH(NH$_2$)CO); 3.5–2.7 (m. 8H. 4CH$_2$N); 1.7–1.3 (m. 10H. 5CH$_2$).

EXAMPLE 3

3-(dimethylamino)propyl Ester of L-NNA

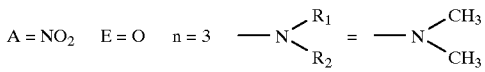

1st Stage:

The corresponding compound of general formula (4) is obtained according to the method as described in example 1, 1st stage, using 3-(dimethylamino)-propanol instead of N-(β-hydroxyethyl)-morpholine. The compound (4) is purified by flash chromatography (CHCl$_3$/EtOH 8:2). A viscous product is obtained.

CCM:rf: 0.17 (CHCl$_3$/MeOH 7:3). RMN$^{-1}$H, 100 MHz, CDCl$_3$, TMS, δppm: 5.4 (d. 1H. NHBoc); 4.2 (m. 3H, COOCH$_2$ and CHNHBoc); 3.4 (m. 2H, NHCH$_2$); 2.3 (m. 8H, CH$_2$N and (CH$_3$)$_2$N): 1.7 (m. 6H, 3CH$_2$).

2nd Stage:

The compound I is obtained in the form of dihydrochloride following the method as described in example 1, 2nd stage.

Melting point: 178 degrees C.—hygroscopic white powder CCM:rf: 0.28 (2-propanol/H$_2$O/NH$_4$OH:7:3:0.1) MH+

(base)=378 RMN$^{-1}$H, 100 MHz, D$_2$O, δppm: 4.15 (m. 3H. CH(NH$_2$)CO, COOCH$_2$); 3.1 (m. 4H, NHCH$_2$ and CH$_2$N); 2.2 (s. 6H, (CH$_3$)N); 1.7 (m. 6H 3CH$_2$).

EXAMPLE 4

Morpholinopropyl Ester of L-NNA

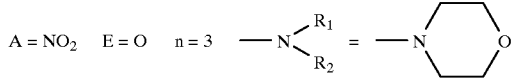

1st Stage:

Operating as described in example 1, 1st stage, but using 3-morpholinopropanol instead of N-(β-hydroxyethyl)-morpholine, the corresponding compound (4) is obtained. The latter is purified by flash chromatography.

Melting point: 106 degrees C. CCM:rf: 0.34 (CHCl$_3$/EtOH 85:15). RMN$^{-1}$H, 100 MHz, CDCl$_3$, TMS, δppm: 7.8 (2H. NH$_2$); 5.4 (d. 1H. NHBoc); 4.3 (m. 3H. CHNHBoc. CO$_2$—CH$_2$) 3.8–3.3 (m. 7H. CH$_2$NH, CH$_2$—O—CH$_2$, NH); 2.4 (m. 6H. 3CH$_2$N); 1.9 (m. 6H. 3CH$_2$); 1.4 (sing. 9H. tBu).

2nd Stage:

The compound I is obtained in the form of dihydrochloride following the method as described in example 1, 2nd stage.

Melting point: 232 degrees C.—hygroscopic white powder CCM:rf: 0.39 (2-propanol/H$_2$O/NH$_4$OH:7:3:0.1) [$_D^{20}$]=+8.2 (H$_2$O) MH+=347 (base) RMN$^{-1}$H, 100 MHz, D$_2$O, δppm: 4.15 (m. 3H, CH(NH$_2$)CO. CO$_2$CH$_2$); 3.9–3.3 (m. 6H, CH$_2$OCH$_2$, CH$_2$NH), 3.1–2.9 (m. 6H, 3CH$_2$N); 2–1.4 (solid, 6H, 3CH$_2$).

EXAMPLE 5

Morpholinohexyl Ester of L-NNA

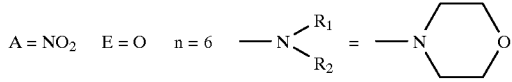

1st Stage:

Operating as described in example 1, 1st stage, but using 6-morpholinohexanol instead of N-(β-hydroxyethyl)-morpholine, the corresponding compound (4) is obtained. The latter is purified by flash chromatography (CHCl$_3$/EtOH 90:10). A viscous product is obtained.

Melting point: 99 degrees C. CCM:rf: 0.32 (CHCl$_3$/EtOH 85:15). RMN$^{-1}$H, 100 MHz, CDCl$_3$, TMS, δppm: 7.7 (2H, NH$_2$): 5.4 (d. 1H, NHBoc); 4.25 (m. 3H, CHNHBoc CO$_2$—CH$_2$) 3.6–3.3 (m. 7H, CH$_2$NH. CH$_2$OCH$_2$. NH); 2.4 (m. 6H, 3CH$_2$N); 1.8–1.3 (solid, 23H, tBu+6CH$_2$).

2nd Stage:

The dihydrochloride of the compound I is obtained according to the method described in example 1, 2nd stage.

Melting point: 214 degrees C.—hygroscopic compound CCM:rf: 0.52 (2-propanol/H$_2$O/NH$_4$OH:7:3:0.1) MH+=389 (base) [$_D^{20}$]=+6.67 (H$_2$O) RMN$^{-1}$H, 100 MHz, D$_2$O, δppm: 4.1 (m. 3H, CH(NH$_2$)CO. CO$_2$CH$_2$); 4–3.3 (solid, 6H, CH$_2$OCH$_2$, CH$_2$NH); 2.1–1.9 (m. 6H, 3CH$_2$N); 1.8–1 (m. 12H, 6CH$_2$).

Example 6

Imidazoloether ester of L-NNA

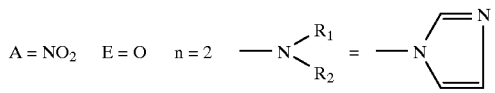

1st Stage:

The corresponding compound (4) is obtained according to the operating mode outlined in Example 1, 1st stage, but by using 2-hydroxyethyl-3 imidazole instead of N-(β-hydroxyethyl)-morpholine. The later is purified in a column of silica (CHCl$_3$/EtOH 9:1 then 88:12).

Melting point: 102 degrees C. CCM:rf: 0.19 (CHCl$_3$/EtOH/NH$_4$OH: 85:15:0.1). RMN$^{-1}$H, 100 MHz, CDCl$_3$, TMS, δppm: 8 (2H, NH2), 7.6 (1H, NH); 7 (d. 2H, imidazole); 5.7 (d. 1H, NHBoc); 4.3–4.1 (m. 5H, CHNHBoc, CO$_2$CH$_2$, CH$_2$-imidazole); 3.3 (d. 2H, CH$_2$NH); 1.4 (m. 13H, tBu, 2CH$_2$).

2nd Stage:

The desired compound I is obtained in the form of dihydrochloride following the method previously described in example 1, 2nd stage.

Melting point: 228 degrees C.—hygroscopic yellow solid MH+=314 (base) CCM:rf: 0.39 (2-propanol/H$_2$O/NH$_4$OH:7:3:0.1). RMN$^{-1}$H, 100 MHz, D$_2$O, δppm: 7.3 (d. 2H, imidazole); 4.4 (m. 4H, CO$_2$CH$_2$ and CH$_2$-imidazole); 4 (t. 1H, CH(NH$_2$)CO); 3.1 (t. 2H, CH$_2$NH); 1.5 (m. 4H, 2CH$_2$).

EXAMPLE 7

Morpholinoethyl Ester of L-arginine.

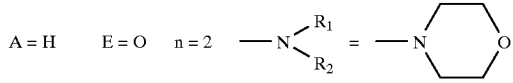

1st Stage:

Operating according to the method previously described (example 1, 1st stage), the corresponding compound (4) is obtained reacting the L-N(Z)-N$_G$-nitroarginine, i.e. the compound II in which the radical R$_3$ represents the Z protector group, with N-(β-hydroxyethyl)-morpholine. The compound is purified by flash chromatography (CHCl$_3$/EtOH 9:1 then 89:11). A viscous product is obtained.

Melting point: 65 degrees C. CCM:Rf: 0.28 (CHCl$_3$/EtOH 85:15) RMN$^{-1}$H, 100 MHz, CDCl$_3$, TMS, δppm: 8.5 (1H, NH); 7.3 (2H, NH$_2$); 7.2 (s. 5H, φ); 5.7 (d. 1H, NHZ), 5 (s. 2H, CH$_2$φ): 4.2 (m. 3H, CHNHZ and CO$_2$CH$_2$); 3.6 (m. 6H, CH$_2$NH and CH$_2$OCH$_2$); 3.4 (1H, NH); 2.4 (m. 6H, 3CH$_2$N); 1.6 (m. 4H, 2CH$_2$).

2nd Stage:

The compound (4) obtained in the previous stages is dissolved in ethanol and subjected to hydrogenolysis; the hydrogenolysis is done in a PARR apparatus in the presence of 10% Pd/C at a pressure of 50 psi at ambient temperature. The disappearance of the precursor is followed by CCM and the reaction ends in four hours. After filtering, the solvent is eliminated at 40 degrees C. The viscous residue is recovered by a minimum of ethanol. 1N hydrochloric acid in diethyl ether is added and it is left stirring for three hours. A precipitate forms little by little. The solid is decanted and washed twice with dry ether. It is dried under reduced pressure and lyophilized. A slightly yellowish product is obtained containing hydrochloric acid which is very hygroscopic.

Melting point: >240 degrees C. (decomposition) MH+= 288 (base) RMN$^{-1}$ H, 100 MHz, D$_2$O, δppm: 4.4 (m. 2H, CO$_2$CH$_2$); 4.1 (t. 1H, CH(NH$_2$)CO); 3.7 (m. 4H, CH$_2$OCH2); 3.4 (m. 4H, CH$_2$N, NHCH$_2$); 3.1 (m. 4H, N(CH$_2$)$_2$); 1.6 (m. 4H, 2CH$_2$).

EXAMPLE 8

Piperidinoethyl Ester of L-arginine.

A = H    E = O    n = 2    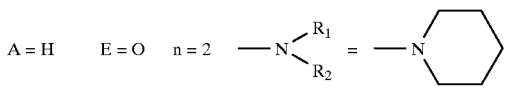

1st Stage:

The corresponding compound of the general formula (4) may be obtained according to the operating method of example 7, 1st stage, but by using N-(β-hydroxyethyl)-piperidine instead of N-(β-hydroxyethyl)-morpholine. The compound can be purified by flash chromatography.

2nd Stage:

The hydrochloride of the compound I may be obtained according to the method previously described (example 7, 2nd stage).

EXAMPLE 9

N-imidazoloethyl Ester of L-arginine.

A = H    E = O    n = 2    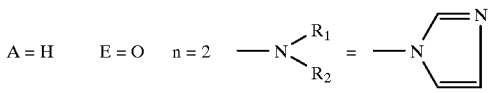

1st Stage:

The corresponding compound of the general formula (4) may be obtained according to the operating method of example 7, 1st stage, but by using N-(β-hydroxyethyl)-piperidine instead of N-(β-hydroxyethyl)-morpholine. The compound can be purified by flash chromatography.

2nd Stage:

The hydrochloride of compound I may be obtained according to the method previously described (example 7, 2nd stage).

EXAMPLE 10

Morpholinoethyl Ester of L-N$^G$-methylarginine (L-NMA).

A = CH$_3$    E = O    n = 2    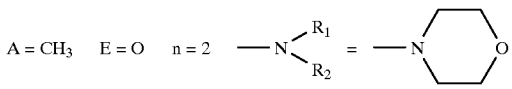

1st Stage:

The corresponding compound of the general formula (4) may be obtained according to the operating method of example 1, 1st stage, by causing a reaction of the L-N(Z)-N$^G$ methylarginine and N-(β-hydroxyethyl)-morpholine. The compound can be purified by chromatography on a silica column.

2nd Stage:

The hydrochloride of compound I may be obtained according to the method described in example 7, 2nd stage.

EXAMPLE 11

Morpholino Amide of L-NNA.

A = NO$_2$    E = covalent bond    n = 0

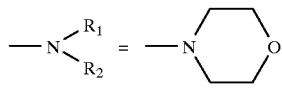

1st Stage: amide of L-NBoc-NG-nitroarginine.

Equimolar quantities of L-N-Boc-N$^G$-nitroarginine, morpholine and 1-hydroxy benzotriazole (HOBT) are dissolved in anhydrous DMF; it is cooled to 0 degrees C. and an equivalent of DDC is added. It is kept at 0 degrees C. for 10 minutes. The reaction is continued for 20 minutes at 0 degrees C., then at ambient temperature for 6 hours. After the usual treatments, an oil which crystalizes is obtained by flash chromatography (eluant CHCl$_3$/MeOH: 95:5).

CCM:rf: 0.66 (CHCl$_3$/MeOH 8:2) IR nujol cm$^{-1}$: γ$_{NH}$: 3400–3300; γ$_{Boc}$ 1700; γ$_{amide}$ 1630 RMN$^{-1}$H, 100 MHz, CDCl$_3$, TMS, δppm: 5.8 (III. d. NHBoc); 3.7 (m. 1H, CHNBoc): 3.5 (solid 4H, 2CH$_2$O); 3.4 (m. 2H, NH—CH$_2$); 2.8 (m. 4H, CH$_2$—N—CH$_2$); 1.7 (m. 4H, CH$_2$CH$_2$); 1.4 (sing. 9H, tBu).

2nd Stage: Deprotection of the NH$_2$ Function.

The product (4) obtained during the previous state is dissolved in anhydrous dichloromethane and 20% trifluoroacetic acid is added. It is stirred at ambient temperature and it is followed by gaseous release. The solvent is eliminated and the residue recovered with water. The solution is passed through an ion exchanger resin. A viscous product is obtained which crystalizes upon the addition of acetone.

Melting point: 246 degrees C. MH+=289 CCM: rf: 0.18 (CHCl$_3$/MeOH 8:2) [α$_D$$^{20}$]=+17.2 (H$_2$O) I.R.: nujol: cm$^{-1}$: γ$_{NH}$ 3400–3300, γ$_{amide}$ 1630 RMN$^{-1}$H, 100 MHz, D$_2$O, δppm: 3.8 (m. 1H, CH(NH$_2$)CO): 3.5 (m. 8H, morpholine); 3.1 (m. 2H, CH$_2$NH); 1.4 (m. 4H, CH$_2$CH$_2$).

EXAMPLE 12

Salt of Ibuprofen and of Morpholino Ethyl Ester of L-N$^G$-nitroarginine

2×10$^{-3}$ M of ibuprofen is dissolved in 15 ml of water containing 2 equivalents of sodium hydroxide; then this solution is added slowly to an aqueous solution (7 ml) of 2×10$^{-3}$ M of morpholinoethyl ester of L-NNA. The mixture grows cloudy; it is heated while stirring to 60 degrees C. for 30 minutes. A clear solution is obtained which after cooling is lyophilized to yield a white powder.

Melting point >260 degrees C.—salt is water soluble RMN$^{-1}$H, 100 MHz, D$_2$O, δppm: 7 (4H, φ); 4.6 (m. 3H, CHNCO and CO$_2$CH$_2$); 3.7–3.4 (m. 6H, 2CH$_2$N); 3–2.9 (m. 4H, N(CH$_2$)$_2$); 2.3 (d. 2H, CH$_2$-φ); 1.7–1.5 (solid, 5H, 2CH$_2$ and 1.2 (d. 3H, CH$_3$); 0.7 (d. 6H, 2CH$_3$).

The ester salt of example 1 with salicylic acid (example 13) and the salt of this same ester with sulindac (example 14) are obtained according to the same method. All of these salts are hygroscopic.

EXAMPLE 15[sic]

Salt of Acetyl Salicylic Acid and of the Morpholino Amide of L-NNA.

The morpholino amide of the L-NNA is dissolved in 30 ml of water. Acetyl salicylic acid is added while stirring and will slowly dissolve in the mixture. Then the clear solution is lyophilized and a white powder is obtained.

Melting point >240 degrees C.—salt is water soluble.

The salts of example 11 with other carboxylic acids such as salicylic acid, sulindac or ibuprofen, may be obtained according to the same method. All of these salts are hygroscopic.

The biological activity of the compounds according to the invention is illustrated by the following tests.

1. Measure of Biological Activity in vitro 1.1. Endothelial constitutive NO synthase The inhibiting properties of constitutive endothelial NO synthase of the products are estimated from their ability to antagonize the dependent endothelium relaxation caused by the carbahol on the isolated aorta of the rat precontracted by phenylephrine (Auguet et al., 1992).

Materials and Methods

The thoracic aorta is extracted from Sprague Dawley male rates (290–350 g) killed by cervical rupture. The aorta is place in the glucosed Krebs Henseleit medium, of the following composition: (mM), NaCl: 118; KCl: 4.7; $MgSO_4$: 1.17; $KH_2PO_4$: 1.18; $CaCl_2$: 2.5; $NaHCO_3$: 25; glucose: 11. This medium is kept at 37 degrees C. and continually traversed by a current of carbogen (95% $O_2$, 5% $CO_2$). After having eliminated the excess conjunctive tissue and fat, the vessels are carefully cut into rings (2 mm wide) and suspended under a tension of 2 grams in 20 ml vats. The recording of the contractions is done using isometric probes connected to a data acquisition system (IOS Dei-Lierre).

Products and Treatment

After an hour of rest, the tonus of the artery is increased by phenylephrine (PE $10_{-6}$ M). When the contraction reaches its maximum (10 minutes), the carbachol ($10_{-5}$ M) is introduced into the vat to check the integrity of the endothelial layer. The preparations are then washed and after 45 minutes of rest, the PE ($10_{-6}$ M) is re-introduced into the bath at the maximum of the contraction; the $10_{-5}$ M carbachol is injected when the maximum relaxation is reached. The tested products are introduced into the bath in cumulative doses.

The results are summarized in Table 1 which follows:

TABLE 1

| Products | $CI_{50}$ ($\mu$M) |
|---|---|
| L-NMMA | 12 |
| L-NA | 7 |
| Aminoguanidine | >100 |
| Example 1 | 10 |
| Example 2 | 30 |
| Example 3 | 75 |
| Example 4 | 10 |
| Example 5 | 5 |
| Example 6 | 80 |
| Example 7 | >100 |
| Example 11 | >100 |
| Example 12 | 5 |
| Example 13 | 10 |
| Example 14 | 9 |

1.2. Neuron constitutive NO synthase

Introduction

The measure of the activity of NO synthase has been done according to the procedure described by Bredt and Snyder (1990).

Materials and Methods

The Sprague Dawley rat cerebellums (280 g. Charles River) were extracted quickly, dried at 4 degrees C. and homogenized in an extraction buffer volume corresponding to 5 ml of HEPES buffer per gram of tissue using Thomas' potter (10 round trips). The homogenates were then centrifuged (21,000 g for 15 minutes at 4 degrees C.).

The floating matter was removed and passed through a column of 1 ml of Dowex AG 50 WX-8 Na+ (BioRad form) previously rinsed with distilled water and by the extraction buffer. After passage through the column, the samples were stored at 4 degrees C. and quickly prepared in doses.

The dosage was done in glass test tubes in which 100 pl of incubation buffer was distributed containing 100 mM of HEPES, pH 7.4 of EDTA, 2.5 mM of CaCl2, 2 mM of dithioreitol, 2 mM of reduced NADPH, 10 $\mu$g/ml of calmoduline and 10 $\mu$M of tetrahydrobiopterine. 25 $\mu$l were added of a solution containing 100 nM of tritiated [labeled with tritium] arginine (specific activity: 56.4 Ci/mmole, Amersham) and 40 $\mu$M of non-radioactive arginine. The reaction is started by adding 50 $\mu$l of homogenate, the final volume being 200 $\mu$l (the missing 25 $\mu$l are either water or a tested product).

After 30 minutes of incubation at ambient temperature the enzyme reaction is stopped by the addition of 2 milliliters of stopping buffer (20 mM of HEPES, pH 5.5; 2 mM EDTA). The samples are passed through 1 ml columns of Dowex AG 50 WX-8 resin. Na+ forms and is eluted with 2 ml of distilled water. After the addition of 10 ml of scintillation liquid, the radioactivity is quantified by means of a liquid scintillation spectrometer. The whites were made according to the same experimental protocol, the 50 $\mu$l of sample being replaced by 50 $\mu$l of extraction buffer. The total radioactivity was determined for each test.

The results are expressed in pmoles of citrulline formed per minute per mg. of proteins The protein concentration was done according to Bradford's method (1976) (Table 2).

TABLE 2

| Products | $CI_{50}$ ($\mu$M) |
|---|---|
| L-NMMA | 2.8 |
| L-NA | 0.6 |
| Aminoguanidine | 510 |
| Example 1 | 2.3 |
| Example 2 | 4 |
| Example 3 | 10 |
| Example 4 | 1.5 |
| Example 5 | 2 |
| Example 6 | 1.8 |
| Example 7 | >10 |
| Example 11 | >300 |
| Example 12 | 0.36 |
| Example 13 | 1 |
| Example 14 | 0.7 |

1.3. Inducible NO synthase

The macrophages produced nitrogen monoxide from an inducible NO synthase by pro-inflammatory stimuli. The macrophage inducible NO synthase is prepared from a homogenate of J774$A_1$ myelomonocyte cells previously stimulated for 48 hours by LPS (E. coli) and by $IFN_\gamma$ Materials and Method 1. Cells: culture and induction of the NO synthase The J774$A_1$ cells (ATCC ref. TIB 67) were cultivated in DMEM at 10% of SVF at 37 degrees C. under an atmosphere of 5% $CO_2$. They were seeded at the rate of $5\times10^3$ cells/cm$^2$ in 150 cm$^2$ flasks. The incubations were done in the presence of LPS (1 pg/ml) and IFN-$\tau$ murin (50 U/ml) in DMEM at 10% of SVF for 24 hours.

2. Preparation of the partially purified NO synthase

The cells were washed with PBS, then put on the Cell Scraper in 4 ml of cold buffer A (4 degrees C.) (buffer A:

hepes 50 mM dithiothreitol 0.5 mM adjusted to pH 4 with NaOH 1N). There were added extemporaneously: pepstatine A 1 mg/ml, leupeptine 1 mg/ml, inhibitor of trypsine from soya 1 mg/ml, antipaine 1 mg/ml, PMSF (Pefobloc) 10 mg/ml.

After centrifuging (1000 g, 4 degrees C., 5 minutes), the centrifuged deposits were collected and put back in 1 ml of buffer A and then sonically treated at 4 degrees C. and the homogenate underwent an ultra-centrifuging (100,000 g, 4 degrees C., 60 minutes). To the material floating on top was added 10% glycerol before freezing at −80 degrees C., it having been previously fractionated. The preparation was tested the same day, but it retained its active nature after ten days of storage at −80 degrees C. A fraction was kept for dosage of proteins by Bradford's micromethod.

3. Enzyme test

The test consisted of the transformation by NO synthase of L-arginine into L-citrulline.

a. Conversion of L-arginine into L-citrulline

Reactional buffer or B buffer: Hepes 100 mM, dithiothreitol 1 mM adjusted to pH 7.4 with NaOH 1N. This buffer was kept several days at 4 degrees C. The NO synthase cofactors were added extemporaneously, namely: 10 $\mu$M tetrahydrobiopterine, 10 $\mu$M FAD, 2 mM NADPH, 2.5 mM $CaCl_2$, 1 mg/ml BSA (in order to make the enzyme soluble). L-arginine solution:

L-arginine ends up at 40 $\mu$M. To continue the reaction an isotope solution was made by adding ($^3$H)-L-arginine to the solution in a final concentration of 100 nM.

Enzyme preparation:

According to a test done previously showing the enzyme activity, the solution was used pure or at 1/10 degree.

Inhibitor:

This was prepared in the B buffer from a concentrated solution in aqueous medium or in DMSO and tested compared with a control without inhibitor. A DMSO control was added where applicable.

Volumes ($\mu$l) used in the test

| Sample | Complete B buffer | Arginine solution | Enzyme preparation | Complete A buffer |
|---|---|---|---|---|
| White | 125 | 25 | — | 50 |
| Control | 125 | 25 | 50 | — |
| Inhibitor | 125 | 25 | 50 | — |

The incubation was done in a double boiler at 37 degrees C. for 15 minutes.

Stopping the reaction:

The reaction was stopped by adding 2 ml of C buffer: 20 mM Hepes, 2 mM EDTA, pH 5.5 adjusted with 1N HCl.

L-arginine and L-citrulline separation:

This was done on 0.5 ml of Dowex 50X-8 (cation exchanger resin) previously brought to equilibrium in buffer C in 2 ml syringes stopped by a glass ball which therefore let only the liquid pass through.

The 50X-8 retained the L-arginine. The sample collected was stored and the rest was eluted from the citrulline by 2 ml of distilled water.

To the 4 ml of aqueous medium were added 16 ml of Instagel Plus and the scintillation flasks were counted a Packard probe.

Calculations:

The following calculation was carried out for each value: [cpm(sample)−cpm(white)]/[cpm(control)−cpm(white)]

The regression line was then plotted in FIG. P 6C and the $CI_{50}$ of the products was determined. The CI50 is the average of two experiments performed on different enzyme preparations. The results are presented in Table 3.

TABLE 3

| Products | $CI_{50}$ ($\mu$M) |
|---|---|
| L-NA | 20.5 |
| L-NMMA | 9.5 |
| Aminoguanidine | 29.6 |
| Example 1 | 29 |
| Example 2 | 53 |
| Example 3 | 30 |
| Example 4 | 110 |
| Example 5 | 380 |
| Example 6 | 15 |
| Example 7 | 22 |
| Example 11 | >300 |
| Example 12 | 40 |
| Example 13 | 28 |
| Example 14 | 38 |

2. In vivo Biological Activity Measurement

Carrageenan edema

Principle

The sub-plantar injection of a suspension of carrageenan, mucopolysaccharides extracted from algae, induces a local inflammatory reaction. Anti-inflammatory compounds are able to antagonize this edema in a different way according to their mode of action (Winter et al., 1962). NO synthase inhibitors have shown a certain effect on this test (Antunes et al., 1991).

Materials and Methods

Lots of 8 Sprague Dawley VAF male rats (Charles River, St. Aubin les Elbeuf of 140 to 215 grams kept fasting for 18 hours were used (n=8).

The edema was obtained by injection in the plantar pulvinus of one of the posterior paws, of a suspension of carrageenan at 1% in physiological serum at the rate of 0.1 ml per animal.

The volume of the paw was measured by plethysmography before, then 1:30 and 3:00 hours after injection of the carrageenan. A percentage of inflammation of the paw was calculated for each animal and each measuring time (water plethysmometer Ugo Basile).

Results

The results are presented in Table 4. (NS=not significant; *=significant; =very significant; *=highly significant).

TABLE 4

| Products | Dose (mg/kg) | Inflammation reduction percentage | |
|---|---|---|---|
| | | 90 min. | 180 min. |
| L-NA | 15 | −60.2** | −52.8** |
| L-NMMA | 15 | −30.5* | −21.9 NS |
| Aminoguanidine | 15 | 9 NS | −13 NS |
| Example 1 | 15 | −62.5** | −55.7** |
| Example 2 | 15 | −58.3** | −56.3** |
| Example 3 | 15 | −48.7** | −61.2** |
| Example 5 | 15 | −75.2** | −48** |
| Example 11 | 15 | +3 NS | −18 NS |
| Example 12 | 15 | −85.9** | −85*** |

We claim:
1. A compound of the formula

I in which:
A is selected from the group consisting of hydrogen, alkyl of 1 to
6 carbon atoms, and nitro,
E is oxygen or a covalent bond,
n is an integer from 1 to 12; and either $R_1$ and $R_2$ represent independently alkyl of 1 to 6 carbon atoms or $R_1$ and $R_2$ form together with the nitrogen atom to which they are attached, a piperidine, morpholine or imedazole ring of 5 or 6 groups containing at least 3 carbon atoms, saturated or unsaturated, of the formula.

2. A compound of claim 1 wherein E is oxygen, A is nitro or hydrogen and $R_1$ and $R_2$ form a morpholine, piperidine, or imidazole ring.

3. A compound according to claim 1 in which E represents a covalent bond, A is $NO_2$ and $R_1$ and $R_2$ form the morpholine ring.

4. Pharmaceutical compositions containing by way of active principle at least one compound of the formula $1_A$:

in which:

A is selected from the group consisting of hydrogen, lower alkyl and $—NO_2$,

E is oxygen or a covalent bond, n is an integer from 1 to 12;

and either $R_1$ and $R_2$ represent independently alkyl of 1 to 6 carbon atoms or form together with the nitrogen atom to which they are attached a piperidine, morphaline or imedazole ring or a salt of this compound, in association with at least one diluting agent or pharmaceutically acceptable vehicle.

5. A method of inhibiting treating inflammation in warm-blooded animals comprising administering to warm-blooded animals an anti-inflammatorily effective amount of a compound of claim 1 to inhibit No synthase activity in the animals.

* * * * *